United States Patent
Tuzsuzov

(10) Patent No.: US 9,139,087 B2
(45) Date of Patent: Sep. 22, 2015

(54) METHOD AND APPARATUS FOR MONITORING AND CONTROL ALERTNESS OF A DRIVER

(75) Inventor: Jordan Tuzsuzov, Karlsruhe (DE)

(73) Assignee: Johnson Controls Automotive Electronics GmbH, Remchingen (DE)

( * ) Notice: Subject to any disclaimer, the term of this patent is extended or adjusted under 35 U.S.C. 154(b) by 129 days.

(21) Appl. No.: 14/003,772

(22) PCT Filed: Mar. 8, 2012

(86) PCT No.: PCT/EP2012/054020
§ 371 (c)(1),
(2), (4) Date: Nov. 8, 2013

(87) PCT Pub. No.: WO2012/123330
PCT Pub. Date: Sep. 20, 2012

(65) Prior Publication Data
US 2014/0167968 A1  Jun. 19, 2014

(30) Foreign Application Priority Data

Mar. 11, 2011  (DE) .......................... 10 2011 013 629
May 6, 2011  (EP) ..................................... 11165175

(51) Int. Cl.
*G08B 23/00* (2006.01)
*B60K 28/06* (2006.01)
(Continued)

(52) U.S. Cl.
CPC ................. *B60K 28/066* (2013.01); *A61B 5/18* (2013.01); *B60W 2040/0872* (2013.01); *B60W 2540/22* (2013.01)

(58) Field of Classification Search
USPC ......... 340/13.36, 438, 439, 539.13, 457, 566, 340/575, 576
See application file for complete search history.

(56) References Cited

U.S. PATENT DOCUMENTS 3,106,981 A * 10/1963 Chakiris ....................... 180/272
3,472,965 A * 10/1969 Blossom ....................... 375/275
(Continued)

FOREIGN PATENT DOCUMENTS

CN  1278090 A  12/2000
CN  101588757 A  11/2009
(Continued)

OTHER PUBLICATIONS

Office Action dated Jan. 6, 2015, in corresponding Japanese Application No. 2013-557099 and English translation, 4 pages.
(Continued)

*Primary Examiner* — Paul Obiniyi
(74) *Attorney, Agent, or Firm* — Foley & Lardner LLP

(57) ABSTRACT

A method for monitoring the alertness of the driver of a vehicle, includes continuously detecting and evaluating at least one physical parameter of the driver while the vehicle is in motion, and transmitting a periodic audio signal with a predetermined frequency into a vehicle interior within a predetermined time period if the evaluated physical parameter is in a critical range, whereby the critical range indicates an appropriate level of fatigue of the driver. An apparatus for monitoring the alertness includes a monitoring unit with a sensor unit, which detects at least one physical parameter of the driver, and an evaluation unit, which evaluates the detected physical parameter while the vehicle is in motion. The evaluation unit is coupled to an audio device, which transmits a periodic audio signal into a vehicle interior within a predetermined time if the evaluated physical parameter is in a critical range.

5 Claims, 2 Drawing Sheets

(51) Int. Cl.
*A61B 5/18* (2006.01)
*B60W 40/08* (2012.01)

(56) References Cited

U.S. PATENT DOCUMENTS

| | | | | |
|---|---|---|---|---|
| 3,577,080 A * | 5/1971 | Cannalte | ............... | 340/13.36 |
| 3,594,772 A * | 7/1971 | Setser | ............... | 180/272 |
| 3,794,969 A * | 2/1974 | Klopfenstein et al. | ............... | 340/439 |
| 3,843,842 A * | 10/1974 | Muller | ............... | 379/74 |
| 3,953,830 A * | 4/1976 | Williams | ............... | 340/438 |
| 3,980,999 A * | 9/1976 | Nishioka et al. | ............... | 340/457 |
| 4,208,654 A * | 6/1980 | Vogt et al. | ............... | 341/20 |
| 4,210,905 A * | 7/1980 | Coons | ............... | 340/575 |
| 4,278,969 A * | 7/1981 | Woods | ............... | 340/576 |
| 4,359,713 A * | 11/1982 | Tsunoda | ............... | 704/274 |
| 4,414,541 A * | 11/1983 | Ho | ............... | 340/566 |
| 4,441,399 A * | 4/1984 | Wiggins et al. | ............... | 84/470 R |
| 4,492,952 A * | 1/1985 | Miller | ............... | 340/439 |
| 4,594,583 A * | 6/1986 | Seko et al. | ............... | 340/576 |
| 4,611,199 A * | 9/1986 | Seko et al. | ............... | 340/576 |
| 4,731,847 A * | 3/1988 | Lybrook et al. | ............... | 704/260 |
| 5,235,124 A * | 8/1993 | Okamura et al. | ............... | 434/307 A |
| 5,471,009 A * | 11/1995 | Oba et al. | ............... | 84/645 |
| 5,521,580 A * | 5/1996 | Kaneko et al. | ............... | 340/439 |
| 5,815,070 A * | 9/1998 | Yoshikawa | ............... | 340/439 |
| 6,226,422 B1 | 5/2001 | Oliver | ............... | 382/313 |
| 6,304,846 B1 * | 10/2001 | George et al. | ............... | 704/270 |
| 6,670,905 B1 | 12/2003 | Orr | ............... | 342/20 |
| 6,721,711 B1 | 4/2004 | Hoshiai | ............... | 704/500 |
| 6,756,903 B2 * | 6/2004 | Omry et al. | ............... | 340/576 |
| 7,010,491 B1 | 3/2006 | Kikumoto | ............... | 704/503 |
| 7,283,056 B2 * | 10/2007 | Bukman et al. | ............... | 340/575 |
| 7,301,465 B2 * | 11/2007 | Tengshe et al. | ............... | 340/575 |
| 7,397,382 B2 * | 7/2008 | Ikegami et al. | ............... | 340/575 |
| 7,427,924 B2 * | 9/2008 | Ferrone et al. | ............... | 340/576 |
| 7,525,034 B2 * | 4/2009 | Nease et al. | ............... | 84/485 R |
| 7,528,731 B2 * | 5/2009 | Zhang et al. | ............... | 340/575 |
| 7,570,785 B2 * | 8/2009 | Breed | ............... | 382/100 |
| 7,663,495 B2 * | 2/2010 | Haque et al. | ............... | 340/576 |
| 7,781,666 B2 * | 8/2010 | Nishitani et al. | ............... | 84/723 |
| 7,977,560 B2 * | 7/2011 | Marcus | ............... | 84/609 |
| 7,978,086 B2 * | 7/2011 | Galley et al. | ............... | 340/576 |
| 8,013,747 B2 * | 9/2011 | Chen | ............... | 340/576 |
| 8,152,198 B2 * | 4/2012 | Breed et al. | ............... | 280/735 |
| 8,519,853 B2 * | 8/2013 | Eskandarian et al. | ............... | 340/575 |
| 8,537,000 B2 * | 9/2013 | Nakagoshi et al. | ............... | 340/539.13 |
| 8,558,141 B2 * | 10/2013 | Byers et al. | ............... | 219/219 |
| 8,570,176 B2 * | 10/2013 | Farbos | ............... | 340/575 |
| 8,587,440 B2 * | 11/2013 | Weng et al. | ............... | 340/575 |
| 8,742,936 B2 * | 6/2014 | Galley et al. | ............... | 340/576 |
| 8,917,182 B2 * | 12/2014 | Chang et al. | ............... | 340/575 |
| 8,963,724 B2 * | 2/2015 | Chang | ............... | 340/575 |
| 2002/0101354 A1* | 8/2002 | Banas | ............... | 340/576 |
| 2004/0090334 A1* | 5/2004 | Zhang et al. | ............... | 340/575 |
| 2006/0050356 A1* | 3/2006 | Varaprasad et al. | ............... | 359/265 |

FOREIGN PATENT DOCUMENTS

| | | | | |
|---|---|---|---|---|
| DE | 10 2007 036 987 A1 | | 2/2009 | |
| GB | 2343578 A | * | 5/2000 | ............ H04N 7/18 |
| JP | 11-033121 A | | 2/1999 | |
| JP | 11-249673 A | | 9/1999 | |
| JP | 2000-264128 A | | 9/2000 | |
| JP | 2004-133749 A | | 4/2004 | |
| JP | 2006-193057 A | | 7/2006 | |
| JP | 2010-253033 A | | 11/2010 | |
| WO | WO-2007/063952 A1 | | 6/2007 | |
| WO | WO-2008/020458 A2 | | 2/2008 | |
| WO | WO 2008020458 A2 | * | 2/2008 | ............ G08B 21/06 |
| WO | WO-2008/090451 A2 | | 7/2008 | |
| WO | WO 2008090451 A2 | * | 7/2008 | ............ A61B 5/18 |

OTHER PUBLICATIONS

Extended European Search Report dated Apr. 23, 2012 as received in European Patent Application No. 11165175.8.
International Search Report dated Apr. 24, 2012 as received in International Application No. PCT/EP2012/054020.
Office Action dated Jun. 3, 2015, received in corresponding Chinese Application No. 201280012891.1, and English translation, 14 pages.

* cited by examiner

METHOD AND APPARATUS FOR MONITORING AND CONTROL ALERTNESS OF A DRIVER

CROSS REFERENCE TO RELATED APPLICATIONS

The present application is a U.S. National Stage of International Application No. PCP/EP2012/054020 filed on Mar. 8, 2012, which claims the benefit of German Patent Application No. 10 2011 013 629.0 filed on Mar. 11, 2011, and European Patent Application No. 11165175.8 filed on May 6, 2011, the entire disclosure of all of which are incorporated herein by reference.

TECHNICAL FIELD

The present invention relates to a method for monitoring the alertness of the driver of a vehicle. Furthermore, the present invention relates to an apparatus for monitoring the alertness of the driver of a vehicle.

BACKGROUND OF THE INVENTION

Monitoring units for monitoring a condition of a driver are well known by prior art. Therefore, at least one sensor, mounted within a motor vehicle, is directed to a driver. As a result physical parameters are detectable, allowing conclusions on a level of awareness and/or fatigue of the driver. For example it is known, that a dizziness of a driver is detectable. In particular, it should be detected, whether the driver is tired and hence an increased accident risk can be assumed. If fatigue is detected, the driver is being warned early and for example asked to stopped to look for a rest.

In addition, motor vehicles are usually equipped with audio facilities, by which it being possible to output songs audibly to entertain vehicle passengers.

It is otherwise known that neural impulses of the human brain have a frequency spectrum, which depends on a condition of the human brain. So-called delta and theta waves are detectable during sleep and have lower frequencies than beta waves, which are detectable when an individual is in a fully awake condition. Scientific studies show, that acoustic and/or optical impulses with respective frequencies can affect a condition of the human brain.

DE 10 2007 036 987 A1 discloses a method and an apparatus for transmitting impact sound into an interior of the motor vehicle by an impact sound generator. The impact sound is transmitted over the impact sound generator to a passenger of the motor vehicle in such a manner that an effect is obtained. The effect is selected from a group of effects comprising the passenger is concentrated by the impact sound, the passenger is prevented from falling asleep, a driving feeling of the passenger is increased, and unwanted vibrations of the motor vehicle are suppressed.

SUMMARY OF THE INVENTION

It is an object of the present invention to provide an improved method and an improved apparatus for monitoring the alertness of the driver of a vehicle.

Preferred embodiments of the invention are given in the dependent claims.

According to the invention, a method for monitoring the alertness of the driver of a vehicle comprises:
continuously detecting and evaluation of at least one physical parameter of the driver while the vehicle is in motion, transmitting a periodic audio signal with a predetermined frequency into a vehicle interior within a predetermined time period if the evaluated physical parameter is in a critical range, whereby the critical range indicates an appropriate level of fatigue of the driver.

A tired driver is one of the important factors that cause traffic accidents. The transmission of a periodic audio signal with a predetermined frequency into a vehicle interior, in particular to the driver, enables an increase of the concentration of the driver, if the driver is tired and hence an increased accident risk can be assumed. With the method according to the invention, the driver is prevented from falling asleep and thus, a drive comfort and drive safety are improved.

According to a preferred embodiment, at least the face of the driver is being detected. The human face indicates more fatigue signs than other human body parts. This fact allows a reliable detection of an appropriate level of fatigue of the driver.

Preferably, the physical parameter is a time period and/or a frequency of an eyelid closure of the driver. The eyelid closure of an individual can be voluntary or involuntary, whereby fatigue affects a slower eyelid closure, in particular a longer time period of eyelid closure, than the eyelid closure of an individual, when it is awake. Thus, a time period and/or a frequency of an eyelid closure are reliable parameters for detection of an appropriate level of fatigue of the driver.

A frequency of the transmitted periodic audio signal is in a frequency range between 12 hertz and 15 hertz and thus in a frequency range of alpha and beta waves of a human brain. Therefore, the transmitted periodic audio signal enables a stimulation of the brain waves of the driver such, that a concentration of the driver can be increased. Furthermore, the frequency of the transmitted periodic audio signal is in a non audible frequency range of an individual, so that the transmitted periodic audio signal has no influence on other vehicle passengers.

In a preferred embodiment, the transmitted periodic audio signal is superimposed with further audio signals. For example, the further audio signals are generated by music reproduction or receiving radio broadcast of an audio device, integrated in the vehicle interior. Preferably, this allows a support of the further audio signals of the audio device, which are usually in an audible range of the driver and other vehicle passengers.

The predetermined time period in which the periodic audio signal is transmitted, ends when the evaluated physical parameter is out of the critical range. That means, that the transmission of the periodic audio signal stops, when the driver is no more tired. This allows that the brain waves of the driver are stimulated as long as the driver is in the critical range, so that the driver is reliably prevented from falling asleep.

An apparatus for monitoring the alertness of the driver of a vehicle, comprises:
a monitoring unit with a sensor unit, which detects at least one physical parameter of the driver, and
an evaluation unit, which evaluates the detected physical parameter while the vehicle is in motion, and whereby the evaluation unit is coupled to an audio device, which transmits a periodic audio signal into a vehicle interior within a predetermined time if the evaluated physical parameter is in a critical range.

The apparatus is well suited to be used as a combination of an audio device coupled with a monitoring unit, which are usually already arranged in modern vehicles. Thus, the apparatus enables a cost-efficient and packaging-optimized solution for monitoring the alertness of the driver of a vehicle, whereby the driver is helped to become awake.

The sensor unit is an optical sensor, by which an appropriate level of fatigue of the driver is reliably detectable, because fatigue signs, especially a longer time period of eyelid closure, are detectable optically best.

Preferably, the sensor unit is arranged into an inside mirror of the vehicle interior. In particular, this allows to detect the face of the driver in a best way, because usually the inside mirror is arranged near the area of a driver's head. Furthermore, the arrangement in the inside mirror enables a packaging-optimized arrangement of the sensor unit in the vehicle interior. Alternatively, the sensor unit is arranged in other suitable places in the vehicle interior, such as instrument panel, steering wheel or even windscreen.

The sensor unit is directed to a driver seat. With this, only the driver is monitored, and stimulated as necessary. Thus, other vehicle passengers are not influenced by the apparatus and may sleep untroubled during a long vehicle drive.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

DETAILED DESCRIPTION OF THE PREFERRED EMBODIMENTS

Figure 1:
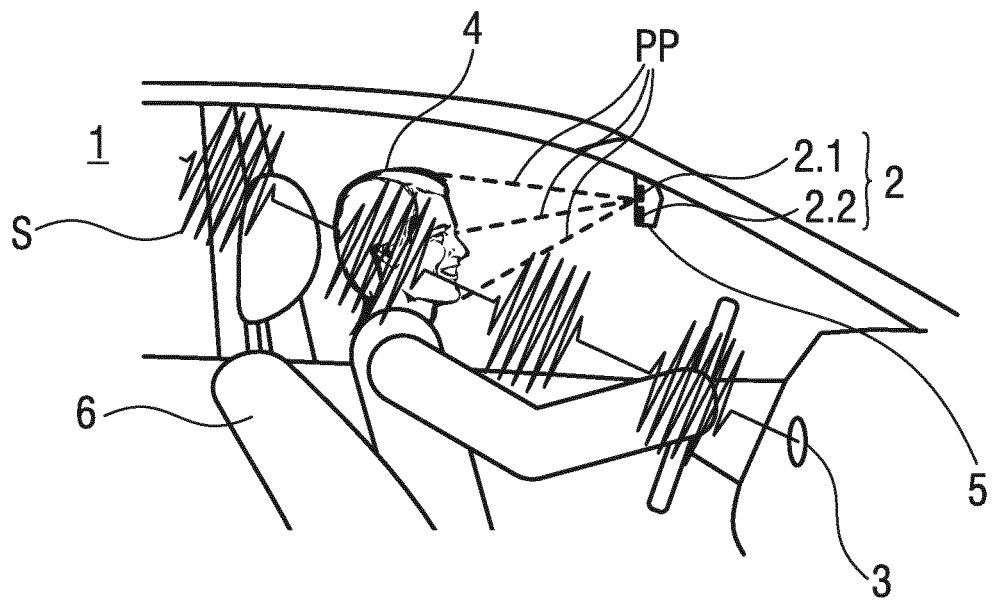
FIG. 1 schematically a side view of a section of a vehicle interior with a monitoring unit and an audio device, FIG. 2 schematically a side view of a section of the vehicle interior 1 with a driver 4, FIG. 3 schematically an exemplary graphic view of human brain waves, and FIG. 4 schematically an exemplary graphic view of a section of an audio signal.

FIG. 1 shows schematically a side view of a section of a vehicle interior 1 of a vehicle with a monitoring unit 2 and an audio device 3.

However, concentrate decrease of a driver 4 as a result of fatigue and, in consequence, decreased ability to respond is a reason for many accidents in traffic. Studies have shown that about 20% of accidents are due to driver fatigue. Thereby for reducing the potential dangers to traffic participants, the present invention involves a method and an apparatus for monitoring the alertness of the driver 4 of a vehicle.

The apparatus comprises the monitoring unit 2, which includes at least one sensor unit 2.1 and an evaluation unit 2.2.

Preferably, the sensor unit 2.1 is an optical sensor, which detects at least one physical parameter PP of the driver 4 continuously while the vehicle is in motion. In a preferred embodiment of the invention, the at least one physical parameter PP is a time period and/or a frequency of an eyelid closure of the driver 4.

The time period and/or the frequency of the eyelid closure are reliable parameters for detection of an appropriate level of fatigue of the driver 4, because fatigue affects a slower eyelid closure, in particular a longer time period of eyelid closure, than the eyelid closure of an individual, when it is awake. Furthermore, the time period and/or the frequency of the eyelid closure are detectable optically best.

Alternatively, the physical parameter PP is a pupil width or a heart beat of the driver 4, whereby the heart beat is not optically detectable. In this alternative embodiment, the sensor unit 2.1 is designed as an electro-mechanical sensor, which is arranged for example in a steering wheel.

In the present embodiment, the sensor unit 2.1 is arranged into an inside mirror 5 of the vehicle interior 1 and directed to a vehicle seat 6. This allows detecting a face or at least suitable parts of the face of the driver 4, if he takes a usual placement on the vehicle seat 6 for driving the vehicle. Thus, the time period and/or the frequency of the eyelid closure are reliably detectable.

Alternatively, the sensor unit 2.1 is arranged in other suitable places inside the vehicle interior 1, such as instrument panel, steering wheel or even windscreen.

The sensor unit 2.1 transmits the continuously detected physical parameter PP to the evaluation unit 2.2, which is designed for example as a microprocessor and also arranged in the inside mirror 5.

After getting the physical parameter PP, the evaluation unit 2.2 evaluates physical parameter PP, for example by using a Kalman Filter, which is integrated as a program sequence in the evaluation unit 2.2. If the evaluation indicates that the physical parameter PP is in a critical range, the evaluation unit 2.2 generates an appropriate signal and transmits this signal to the audio device 3.

In this case the critical range indicates an appropriate level of fatigue of the driver 4, in which a concentration of the driver 4 is decreased, so that an increased accident risk can be assumed. For example, the eyes of the driver 4 are closed over a time of two seconds. For this example, the two seconds are a limit for the critical range.

After getting the transmitted signal of the evaluation unit 2.2, the audio device 3 processes the signal and transmits the signal as a periodic audio signal S into the vehicle interior 1, in particular directed to the driver 4.

Figure 3:
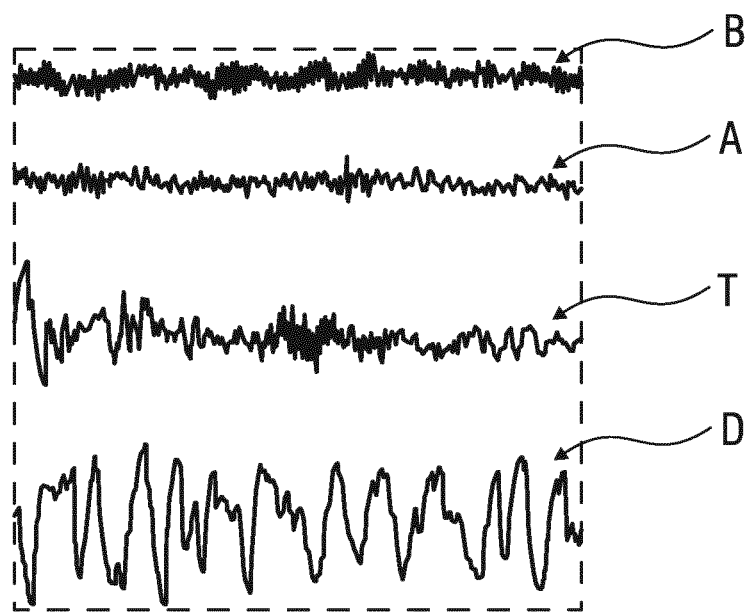

Preferably, a frequency of the audio signal S is in a frequency range between 12 hertz and 15 hertz and thus in a frequency range of alpha waves and beta waves of a human brain, which are shown in FIG. 3 more detailed. The transmitted periodic audio signal S is transmitted as monaural beats or binaural beats or isochronic beats. Monaural beats are a result of an arithmetic sum of waveforms of two tones as they add or subtract from one another, becoming louder and quieter. That means that they are constant sine wave pulses. Binaural beats are perceived by presenting two different tones at slightly different frequencies separately into each ear of the driver 4. In the present embodiment, the audio signal S is designed as an isochronic beat. Isochronic beats are regular beats of a single tone.

Furthermore, the frequency of the audio signal S is in a non audible frequency range of an individual, so that the audio signal S has no influence on other vehicle passengers.

Therefore, the audio signal S enables a stimulation of the brain waves of the driver 4 such, that a concentration of the driver 4 is increasable.

In a preferred embodiment, the audio signal S is superimposed with further audio signals. For example, the further audio signals are generated by music reproduction or receiving radio broadcast of the audio device 3. Preferably, this allows a support of the further audio signals of the audio device 3 to improve a sound of the audio device 3.

The audio signal S is transmitted in a predetermined time period, which ends when the evaluated physical parameter PP is out of the critical range. That means, that the transmission of the audio signal S stops, when the driver 4 is no more tired. This allows a stimulation of the brain waves of the driver 4 as long as the concentration of the driver 4 is decreased. Thus, the driver 4 is reliably prevented from falling asleep.

Figure 2:
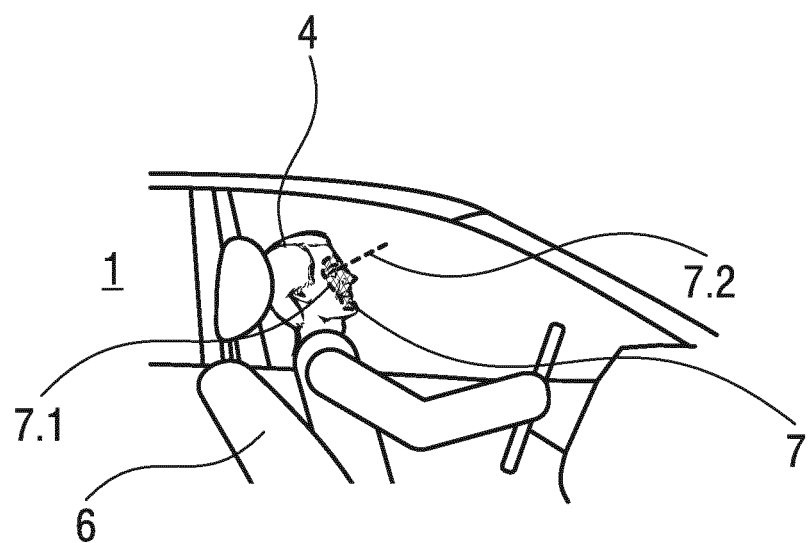

FIG. 2 shows schematically a side view of a section of the vehicle interior 1 with the driver 4.

In the face of the driver 4 a mark 7 is shown, which is bordered by a first dashed line 7.1. The mark 7 represents a detection area of the sensor unit 2.1. A second dashed line 7.2 is perpendicular onto an eye of the driver 4 and represents the detection of an eyelid closure as a physical parameter PP for a reliable detection of an appropriate level of fatigue of the driver 4.

For example, the face is located using a so-called "Haar algorithm", which is integrated as a program sequence in the evaluation unit 2.2. The eye location of the driver 4 can be found for example with projection techniques.

The human face indicates more fatigue signs than other human body parts. This fact allows a reliable detection of an appropriate level of fatigue of the driver 4, so that the brain waves of the driver 4 can be stimulated, if he indicates a decrease of concentration.

FIG. 3 shows exemplary a graphic view of such brain waves.

Depending on their frequency brain waves are classified as beta waves B, alpha waves A, theta waves T and delta waves D, which are shown in this sequence from top to down in the present drawing.

Delta waves D are in a frequency range from 1 Hertz to 4 Hertz. They have high amplitudes and slow waves. Usually, they appear when the brain rests, in particular when an individual is in a slow wave sleep.

Theta waves T are in a frequency range from 4 Hertz to 7 Hertz. They appear usually when an individual is drowsy or in a sleep latency.

Alpha waves A are in a frequency range from 8 Hertz to 12 Hertz. They appear usually when an individual closes the eyes and is in relaxation, and attenuates with eye opening or mental exertion.

Beta waves B are in a frequency range from 12 Hertz to about 30 Hertz. They appear usually when an individual is fully awake and highly concentrated.

With the audio signal S, the brain waves are such stimulated, that a tired driver 4 with theta waves T preferably becomes a full concentrated driver 4 with high alpha waves A or low beta waves B.

Figure 4:
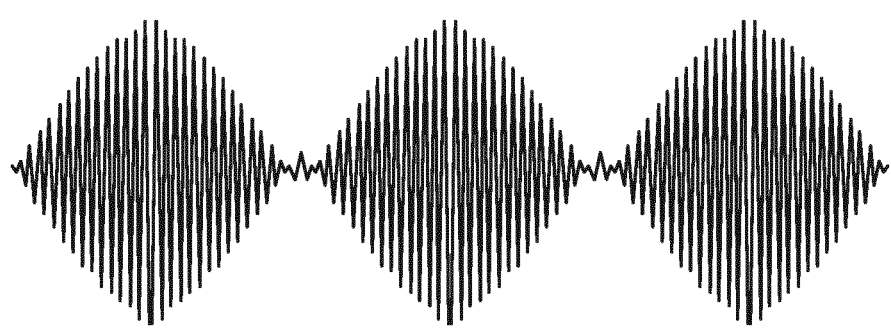

FIG. 4 shows an example of a section of such an audio signal S.

The audio signal S is amplitude and/or frequency modulated and designed as a monaural beat.

The audio signal S effects a stimulation of the brain waves of the driver 4 as described in FIGS. 1 to 3.

The periodic characteristic of the audio signal S enables a continuous and uniform stimulation of the brain waves of the driver 4 until he is awake with full concentration.

LIST OF REFERENCES 1 vehicle interior
2 monitoring unit
2.1 sensor unit
2.2 evaluation unit
3 audio device
4 driver
5 inside mirror
6 driver seat
7 mark
7.1 first dashed line
7.2 second dashed line
A alpha waves
B beta waves
D delta waves
PP physical parameter
S audio signal
T theta waves

The invention claimed is:

1. A method for monitoring the alertness of the driver of a vehicle, comprising:
continuously detecting and evaluating at least one physical parameter of the driver while the vehicle is in motion; transmitting a periodic audio signal with a predetermined frequency into a vehicle interior within a predetermined time period if the evaluated physical parameter is in a critical range, whereby the critical range indicates an appropriate level of fatigue of the driver, wherein the predetermined time period ends when the evaluated physical parameter is out of the critical range, wherein the physical parameter is at least one of a time period and a frequency of an eyelid closure of the driver, wherein the predetermined frequency of the transmitted periodic audio signal is in a frequency range between 12 hertz and 15 hertz, wherein the transmitted periodic audio signal is superimposed with other audio signals, wherein the sensor unit is arranged in an inside mirror of the vehicle interior.

2. The method according to claim 1, comprising: detecting as one physical parameter the face of the driver.

3. An apparatus for monitoring the alertness of the driver of a vehicle, comprising: a monitoring unit with a sensor unit, which detects at least one physical parameter of the driver; and an evaluation unit, which evaluates the detected physical parameter while the vehicle is in motion; wherein the evaluation unit is coupled to an audio device, which transmits a periodic audio signal into a vehicle interior within a predetermined time if the evaluated physical parameter is in a critical range, wherein the predetermined time period ends when the evaluated physical parameter is out of the critical range, wherein the physical parameter is at least one of a time period and a frequency of an eyelid closure of the driver, wherein the predetermined frequency of the transmitted periodic audio signal is in a frequency range between 12 hertz and 15 hertz, wherein the transmitted periodic audio signal is superimposed with other audio signals, wherein the sensor unit is arranged in an inside mirror of the vehicle interior.

4. The apparatus according to claim 3, wherein the sensor unit is an optical sensor.

5. The apparatus according to claim 3, wherein the sensor unit is directed toward a driver seat.

* * * * *